United States Patent [19]
Bruce

[11] Patent Number: 6,074,060
[45] Date of Patent: Jun. 13, 2000

[54] EYESIGHT AND HEARING SAFETY APPARATUS

[76] Inventor: Joe A. Bruce, 7825 Jackson Rd., Beaumont, Tex. 77706

[21] Appl. No.: 09/414,088

[22] Filed: Oct. 7, 1999

Related U.S. Application Data

[60] Provisional application No. 60/113,972, Dec. 28, 1998.

[51] Int. Cl.[7] .................................................. G02C 1/00
[52] U.S. Cl. ............................................................ 351/158
[58] Field of Search .................................. 351/158, 123; 2/423

[56] References Cited

U.S. PATENT DOCUMENTS

| | | | |
|---|---|---|---|
| D. 262,491 | 12/1981 | Ebert | D24/67 |
| D. 282,308 | 1/1986 | Kain | D2/247 |
| D. 371,150 | 6/1996 | Bolash, IV | D16/339 |
| 3,856,007 | 12/1974 | Leight | 351/158 |
| 3,943,925 | 3/1976 | Leight | 351/158 |
| 5,278,999 | 1/1994 | Brown et al. | 2/209 |
| 5,475,449 | 12/1995 | Pyle | 351/123 |
| 5,541,677 | 7/1996 | Huhtala | 351/156 |
| 5,619,750 | 4/1997 | Allewalt | 2/13 |
| 5,668,354 | 9/1997 | Falco | 181/135 |
| 5,703,670 | 12/1997 | Callard | 351/158 |
| 5,717,479 | 2/1998 | Rickards | 351/158 |
| 5,718,002 | 2/1998 | Pavlak | 2/423 |
| 5,781,272 | 7/1998 | Bright et al. | 351/123 |

FOREIGN PATENT DOCUMENTS

| | | |
|---|---|---|
| 2559279 | 2/1984 | France . |
| 61536 | 3/1992 | Germany . |

OTHER PUBLICATIONS

N.Y. Daily News, Mar. 1956, magazine section.

*Primary Examiner*—Huy Mai
*Attorney, Agent, or Firm*—Richard C. Litman

[57] ABSTRACT

An eyesight and hearing safety apparatus for protecting a person's eyes and hearing. The eyesight and hearing safety apparatus of the present invention is generally defined by a frame, at least one eye shield, two temple members, two cords, and two ear protectors. The two temple members are each pivotally attached to opposing ends of the frame for enabling the frame to be supported from a person's ears. The frame has at least one eye shield formed therein for shielding a person's eyes from flying projectiles when the frame is worn over the nose a person. One end of each cord is affixed to one of the temple members for providing a flexible means of suspension from the frame. Each ear protector is attached the opposing end of each cord for attaching each protector to the frame.

3 Claims, 2 Drawing Sheets

EYESIGHT AND HEARING SAFETY APPARATUS

CROSS-REFERENCE TO RELATED APPLICATION

This application claims the benefit of U.S. Provisional Patent Application Ser. No. 60/113,972, filed Dec. 28, 1998.

BACKGROUND OF THE INVENTION

1. FIELD OF THE INVENTION

The present invention relates generally to safety devices, and in particular, to devices which protect the eyesight and hearing of a human being from injury.

2. DESCRIPTION OF RELATED ART

It is often desired to protect the eyes of a human being from being injured by flying debris at the workplace and to protect the hearing of a human being from being injured due to excessive noise at the workplace. Well-known solutions for this problem include providing separate safety glasses and earplugs; however, in practice, such as when an employee must daily provide or repeatedly remember to don such protection, the problem of loss of separate protection devices may lead to lost work time or other inconvenience until proper protection in the work environment can be restored.

Well-known solutions for this problem include providing safety glasses with earplugs attached to the safety glasses in some manner. For example, U.S. Pat. No. 5,278,999 issued to Brown et al. discloses an improved combined ear and eye shield that includes a head support independent of the eye shield. U.S. Pat. No. 5,475,449 issued to Pyle on Dec. 12, 1995 discloses a device which removably secures a standard set of earplugs to a pair of eyeglasses, preferably safety glasses, by double looping a standard cord with a pair of cord adjusters. U.S. Pat. No. 5,717,479 issued to Rickards on Feb. 10, 1998 discloses an industrial safety assembly including a front frame member having a transparent shatterproof eye panel and protective inserts removably secured thereto for shielding a wearer's eyes and for muffling exterior noise. U.S. Pat. No. 5,718,002 issued to Pavlak discloses eye and ear protective eye-wear comprising a standard pair of conventional reading glasses, prescription glasses, safety glasses or sunglasses to which a pair of wind-deflecting deflectors are attached to the lenses and/or frame and extend rearward from the lenses toward the ear. U.S. Pat. No. 5,781,272 issued to Bright et al. on Jul. 14, 1998 discloses an eyesight and hearing apparatus comprising a front guard portion defined by a front transparent panel and a first and second earplug.

However, none of the aforementioned inventions disclose a combination safety glasses and an hearing protective device defined by a pair of earplugs permanently affixed to a conventional eyeglass frame by a flexible tether for preventing removal of the earplugs from the eyeglasses frame. None of the above inventions and patents, taken either singly or in combination, is seen to describe the instant invention as claimed.

SUMMARY OF THE INVENTION

The present invention is an eyesight and hearing safety apparatus generally defined by an eyeglasses frame including protective lenses or other shield and two temple members, two tethers or cords depending from the temple members, and two ear protectors, such as foam earplugs, each terminally attached to a tether. As is conventional, the two temple members are each pivotally attached to opposing ends of the frame for enabling the frame to be supported from a person's ears, and for folded storage when not in use. The eye shield is shatter resistant and inserts into the frame for shielding the wearer's eyes from flying projectiles when the frame is worn by the wearer. One end of each tether or cord is affixed to one of the temple members for providing a flexible means of suspension of each ear protector from the frame, and the other end is attached to an ear protector. Thus, the ear protectors and the eye shields remain united and less likely to be individually misplaced.

Accordingly, it is a principal object of the invention to provide a combination eye and hearing protection device having both eye protection means and hearing protection means, wherein the hearing protection means is undetachably affixed to the eye protection means for insuring availability of both an eye protection means and a hearing protection means.

It is another object of the invention to provide a combination eye and hearing protection device having a simple construction.

It is a further object of the invention to provide a combination eye and hearing protection device that is cheaper to manufacture than comparable known combination eye and ear protection devices.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
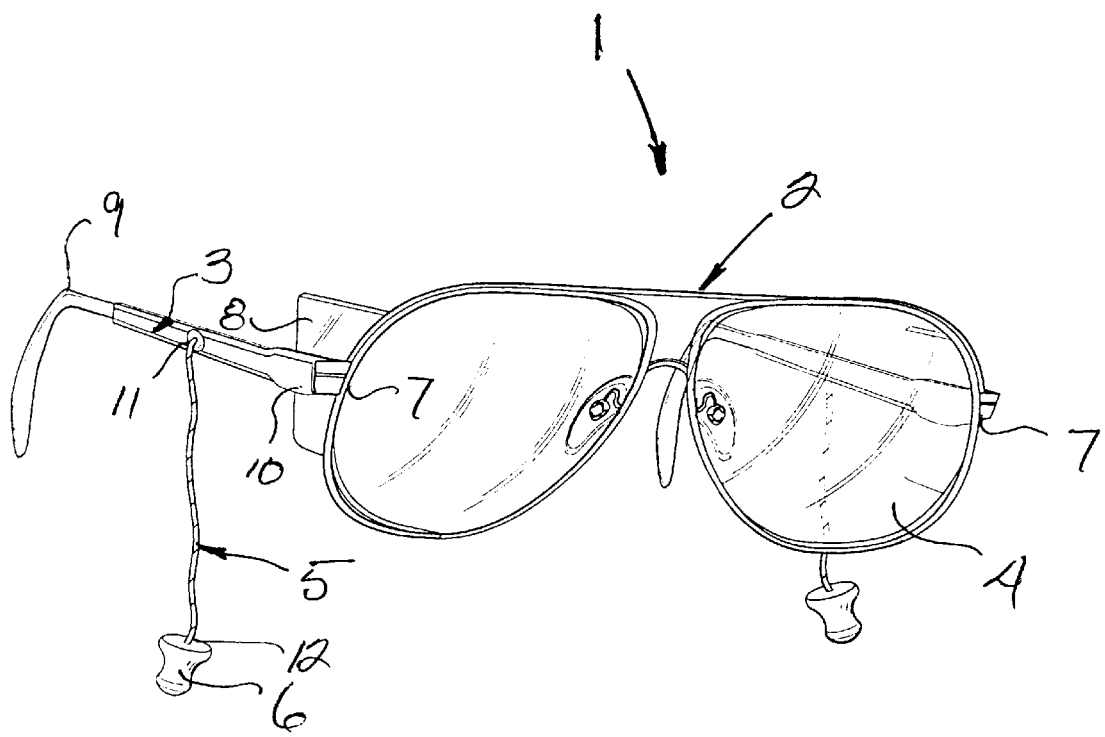
FIG. 1 is an perspective view of safety glasses with earplugs according to the present invention.

The present invention is a combined eyesight and hearing safety apparatus for protecting a person's eyesight and hearing. FIG. 1 shows a perspective view of a combined eyesight and hearing apparatus 1 according to a preferred embodiment of the invention. The combined eyesight and hearing apparatus 1 is generally defined by a frame 2, two temple members 3, an eye shield or protective lens 4 for each eye, two tethers or cords 5, and two ear protectors 6. Alternatively, the combined eyesight and hearing apparatus 1 may have a unitary eye shield (not shown) for shielding each eye of a wearer, the shield defining a generally v-shaped cutout for placement on the bridge of the nose.

Preferably, the frame 2 is a conventional frame configured for accommodating an eye shield 4 for shielding a wearer's eyes from flying debris. The eye shield 4 is made of a transparent material, such as a plastic material, both enabling a wearer to see therethrough while also resisting fracturing and shattering when subject to a sudden impact (e.g., when dropped or struck by flying debris).

The frame 2, having opposing ends 7, further includes a temple member 3 attached to each end 7, enabling the frame 2 to be supportable from a person's ears. More specifically, each temple member 3 comprises an attachment end 10 and a support end 9. Each temple member 3 is preferably pivotally attached to the frame 2 at one of the opposing ends 7 by the attachment end 10, thus enabling the temple member 3 to be folded against the frame 2 when the frame 2 is not being worn by a person. Accordingly, the frame 2 may be positioned in a folded configuration when not being worn to consume less space than when the temple members 3 are positioned in an extended configuration. Any well known hinge means may be used for pivotally attach the temple member 3 to the frame 2.

The combined eyesight and hearing apparatus 1 may further include a side eye shield 8 attached to each temple member 3 near the attachment end 10, for shielding the sides of the wearer's eyes from flying projectiles. The side eye shield 8 is made of a transparent, shatter resistant material, as suggested above, while not obstructing the wearer's peripheral view.

Each of the two tethers is typically a cord 5, defining a first end 11 and a second end 12. Preferably, each cord is approximately 3-½ inches in length. The first end 11 is fixedly attached to the temple member 3 for providing a flexible means of attaching an earplug to the frame 2. One of the ear protectors 6 is fixedly attached to each second end 12 for attaching an ear protector to the frame 2. This configuration prevents the ear protectors 6 from getting separated from the eye shield 8, thereby reducing the likelihood of misplacement of either the eyesight protector or hearing protector.

Figure 2:
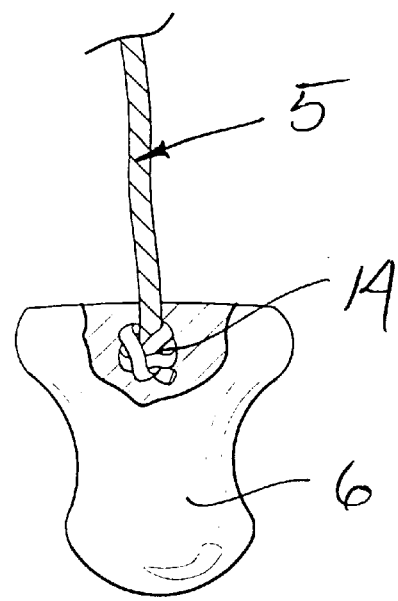
FIG. 2 is an enlarged, partially fragmented, view of one of the earplugs according to a preferred embodiment of the present invention.
Figure 3:
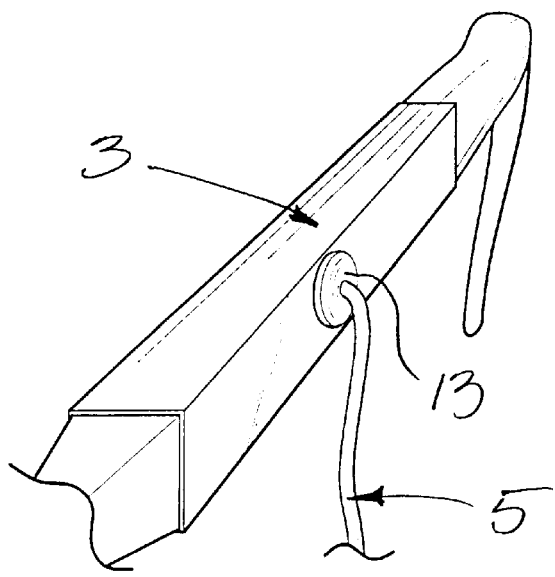
FIG. 3 is an enlarged perspective view of an earplug attached to a temple member according to a preferred embodiment of the present invention.

Further details relating to a preferred means for attachment of the first end 11 to the temple member 3 may best be appreciated by referring to FIGS. 2 and 3. FIG. 3 shows an enlarged view of the ear protector 6 and temple member 3 attachment. Preferably, the first end 11 is molded to the temple member 3 by any well-known molding means. As shown, formed around the first end 11 of the cord 5 is a circular mound 13 attaching the first end 11 to the temple member 3. The mound 13 may be attached integrally in the temple member 3 by thermo-plastic welding techniques, or, may be adhesively attached to the temple member 3 by well-known adhesive means.

Further details relating to attachment of the ear protector 6 to the cord 5 will now be described. Each of the cords 5 has a knot 14 formed at the second end 12. Formed integrally and entirely around each knot 14 is the ear protector 6. The ear protector 6 is preferably a conventional ear plug made of a washable material, such as a foamed rubber material, foamed closed-cell polyurethane, or silicone. Disposable earplugs currently commercially available are well known which have resilience and shape-memory that, upon compression of the foam, permits a slowed expansion which over a period of minutes fully expands the plug against the ear canal for a tight fit. Such material may easily be molded to house the knot 14, which serves to form an enlarged portion in the cord 5 for providing added resistance against removal of the tether from the plug.

It is to be understood that the present invention is not limited to the sole embodiments described above, but encompasses any and all embodiments within the scope of the following claims.

I claim:

1. An eyesight and hearing safety apparatus for use by a person, said apparatus comprising:

a frame having at least one eye shield formed therein for shielding a wearer's eyes;

two temple members, each pivotally attached to one end of said frame for supporting said frame from an individual's ears;

two cords, each having a first end and a second end, said first end is affixed to one of said two temple members for providing a means for flexibly supporting an ear protector from said frame; and two ear protectors, each attached to said second end for attaching each ear protector to said frame.

2. The eyesight and hearing safety apparatus according to claim 1, wherein each of said two ear protectors are a foamed ear plug, said second end of said cord including an enlarged portion, and said foamed ear plug being formed around said enlarged portion.

3. The eyesight and hearing safety apparatus according to claim 2, wherein said enlarged portion is a knot.

* * * * *